(12) United States Patent
Yatsuka et al.

(10) Patent No.: US 6,613,897 B1
(45) Date of Patent: Sep. 2, 2003

(54) COMPOUNDS HAVING GLUCURONIC ACID DERIVATIVES AND GLUCOSAMINE DERIVATIVE IN THE STRUCTURE, PROCESS FOR PRODUCING THE SAME AND UTILIZATION THEREOF

(75) Inventors: Nobuaki Yatsuka, Ibaraki (JP); Nobuyuki Sato, Ibaraki (JP); Shigeru Moriyama, Ibaraki (JP); Tadakazu Tamai, Ibaraki (JP); Masazumi Nishikawa, Ibaraki (JP)

(73) Assignee: Maruha Corporation, Tokyo (JP)

( * ) Notice: Subject to any disclaimer, the term of this patent is extended or adjusted under 35 U.S.C. 154(b) by 0 days.

(21) Appl. No.: 09/674,252

(22) PCT Filed: Apr. 30, 1999

(86) PCT No.: PCT/JP99/02306

§ 371 (c)(1),
(2), (4) Date: Oct. 30, 2000

(87) PCT Pub. No.: WO99/57301

PCT Pub. Date: Nov. 11, 1999

(30) Foreign Application Priority Data

Apr. 30, 1998 (JP) .......................................... 10-120425
Sep. 28, 1998 (JP) .......................................... 10-273895

(51) Int. Cl.$^7$ .......................... A61K 31/70; C08G 63/91
(52) U.S. Cl. ..................... 536/123.1; 536/4.1; 536/119; 536/18.7; 514/25; 514/822; 514/54; 435/101
(58) Field of Search .......................... 514/25, 822, 54; 536/123.1, 4.1, 119, 18.7; 435/101

(56) References Cited

U.S. PATENT DOCUMENTS

| | | | |
|---|---|---|---|
| 4,258,134 A | | 3/1981 | Yoshida et al. |
| 4,820,516 A | | 4/1989 | Sawyer et al. |
| 5,008,253 A | | 4/1991 | Casu et al. |
| 5,510,418 A | * | 4/1996 | Rhee et al. ................. 525/54.2 |
| 5,585,361 A | * | 12/1996 | Burns et al. .................... 514/25 |
| 5,644,049 A | | 7/1997 | Giusti et al. |

FOREIGN PATENT DOCUMENTS

| | | | |
|---|---|---|---|
| EP | 0 295 092 A2 | | 12/1988 |
| EP | 0 686 395 A2 | | 12/1995 |
| JP | 6-73103 | | 3/1994 |
| JP | 7-278203 | | 10/1995 |
| SL | CS 264719 | * | 9/1989 |
| WO | WO96/24392 | | 8/1996 |
| WO | 96/28730 | | 9/1996 |

OTHER PUBLICATIONS

Miyamoto et al., "Purification and characterization of hyaluronic acid from the horny layer of guinea pigs." J. Biochem. (Tokyo), 1984, 95(5), pp. 1331–6.*
Radaeva et al., "Hyaluronic acid: biological role, structure, synthesis, isolation, purification and application." Prikl. Biokhim. Mikrobiol., 1997, 33(2), pp. 133–137.*
Benedetti et al. "Biocompatibility and biodegradation of different hyaluronan derivatives (Hyaff) implanted rats." Biomaterials, (Dec. 1993), 14(15), pp. 1154–1160.*
Carbohydr. Res. 288 (1996) Blatter G. et al., "The use of 2–deoxy–2–trichloroacetamido–D–glucopyranose derivatives in syntheses of hyaluronic acid–related tetra–, hexa–, and octa–saccharides having a methyl beta–D–glucopyrannosidronic acid at the reducing end" P.109–125.
Int. J. Cancer 71 (1997) Deep R. et al., "Early–response gene signaling is induced by angiogenic oligosaccharides of hyaluronan in endothlial cells. Inhibition by non–angiogenic, high–molecular–weight hyaluronan" P. 251–256.
Blatter, G. et al., Carbohydrate Research, vol. 288, pp. 109–125 (1996).
Kenneth N. Price et al., Carbohydrate Research, vol. 303, pp. 301–311 (1997).
Eiji Shimada et al., J. Biochem, vol. 96, pp. 721–725 (1984).
James E. Christner et al., The Journal of Biological Chemistry, vol. 254, No. 11, pp. 4624–4630, (1979).
Eiji Shimada et al., Journal of Biochemistry, vol. 88, pp. 1015–1023 (1980).
Koen M. Halkes et al., Carbohydrate Research, vol. 309, pp. 161–174 (1998).
West et al., "Angiogenesis Induced by Degradation Products of Hyaluronic Acid", *Science,* vol. 228, Jun. 14, 1985, pp. 1324–1326.

(List continued on next page.)

*Primary Examiner*—Samuel Barts
*Assistant Examiner*—Devesh Khare
(74) *Attorney, Agent, or Firm*—Birch, Stewart, Kolasch & Birch, LLP

(57) ABSTRACT

①Compounds of the following general formula (1) having a glucuronic acid derivative and a glucosamine derivative in the structure thereof, pharmacologically acceptable salts and solvates of the compounds, or solvates of the salts, ② a method for producing the compounds ①, ③ a pharmaceutical composition containing the compounds ①, ④ polymers having at least one of the compounds ① as a side chain structure, ⑤ a coating agent containing the compound ① or the polymer as one of active ingredients, and ⑥ molded products, artificial organs, medical devices, and equipment for cell culture, which have been produced using the polymer ④ and/or the coating agent ⑤.

Formula (1)

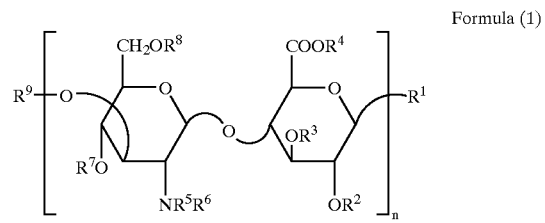

41 Claims, No Drawings

OTHER PUBLICATIONS

West et al., "The Effect of Hyaluronate and Its Oligosaccharides on Endothelial Cell Proliferation and Monolayer Integrity", *Experimental Cell Research,* vol. 183, 1989, pp. 179–196.

Sattar et al., "Does Hyaluronan Have a Role in Endothelial Cell Proliferation of the Synovium?", *Seminars in Arthritis and Rheumatism,* vol. 22, No. 1, Aug. 1992, pp. 37–43.

Sattar, et al., "Application of Angiogenic Oligosaccharides of Hyaluronan Increases Blood Vessel Numbers in Rat Skin", *The Journal of Investigative Dermatology,* vol. 103, No. 4, Oct. 1994, pp. 576–579.

Lees et al., "Angiogenesis in a Delayed Revascularization Model Is Accelerated by Angiogenic Oligosaccharides of Hyaluronan", *Laboratory Investigation,* vol. 73, No. 2, 1995, pp. 259–266.

Lokeshwar et al., "The Cell Adhesion Molecule, GP116, Is a New CD44 Variant (ex14/v10) Involved in Hyaluronic Acid Binding and Endothelial Cell Proliferation", *The Journal of Biological Chemistry,* vol. 271, No. 39, Sep. 27, 1996, pp. 23853–23864.

Montesano et al., "Synergistic Effect of Hyaluronan Oligosaccharides and Vascular Endothelial Growth Factor on Angiogenesis In Vitro", *Laboratory Investigation,* vol. 75, No. 2, Aug. 1996, pp. 249–262.

Trochon et al., "Evidence of Involvement of CD44 in Endothelial Cell . . . ", *Int. J. Cancer,* vol. 66, 1996, pp. 664–668.

Rahmanian et al., "Hyaluronan Oligosaccharides Induce Tube . . . ", *Experimental Cell Research,* vol. 237, 1997, pp. 223–230, Article No. EX973792.

Trochon et al., "Hyaluronectin blocks the stimulatory effect of hyaluronan . . . ", *FEBS Letters,* vol. 418, 1997, pp. 6–10.

Deed et al., "Early–Response Gene Signalling is Induced by Angiogenic . . . ", *Int. J. Cancer,* vol. 71, 1997, pp. 251–256.

* cited by examiner

COMPOUNDS HAVING GLUCURONIC ACID DERIVATIVES AND GLUCOSAMINE DERIVATIVE IN THE STRUCTURE, PROCESS FOR PRODUCING THE SAME AND UTILIZATION THEREOF

This application is the national phase under 35 U.S.C. § 371 of PCT International Application No. PCT/JP99/02306 which has an International filing date of Apr. 30, 1999, which designated the United States of America.

TECHNICAL FIELD

This invention relates to novel compounds having a glucuronic acid derivative and a glucosamine derivative in their structure, a method for producing the compounds, a pharmaceutical composition containing the compounds and polymers having the compounds in their side chain structure, molded products produced using them, and artificial organs, medical devices, and cell culture equipment produced by use of the molded products as components.

BACKGROUND ART

Thrombosis has become one of the major causes of it deaths in Western countries and in Japan in recent years. It is the predominant cause of death surpassing cancer, if the causes include arterial diseases such as myocardial infarction and cerebral infarction. Various factors are involved in thrombosis, and vascular lesions such as arteriosclerosis often form the basis for thrombosis. A normal blood vessel is made highly antithrombotic by vascular endothelial cells. However, platelets adhere to activated vascular endothelial cells at the site of a vascular lesion, such as a focus of arteriosclerosis, or to vascular subendothelial tissue exposed by damage, so that pathological thrombus tends to form. As drugs for suppressing pathological thrombus formation, drugs for suppressing adhesion or aggregation of platelets, i.e., "antiplatelet agents", have attracted attention, and have found wide clinical use. The history of antiplatelet agents is relatively recent, and the development of better drugs of this type is expected.

As described above, the normal blood vessel is made highly antithrombotic by vascular endothelial cells. The roles of the vascular endothelial cells will be discussed more closely. The vascular endothelial cells are a group of single-layered cells which continuously cover the systemic vascular lumina. Normal vascular endothelial cells play a wide variety of roles, such as ① suppression vascular permeability, ② anti-thrombosing of vascular lumen, ③ regulation of relaxation and contraction of vascular smooth muscle, and ④ control of wandering or growth of vascular mural cells. Thus, vascular endothelial cells are said to be of central importance in making blood vessels as such.

Humans are said to age with blood vessels, and vascular walls are damaged with age. When a vascular wall is damaged and ruptured, the rhexis of the blood vessel appears as cardiovascular disease, such as myocardial infarction, aortic aneurysm, cerebral apoplexy, or necrosis. The most prominent cause of vascular wall rupture is arteriosclerosis.

The-current treatments or prophylaxes of arteriosclerosis are mostly approaches from the aspect of improvement of lipid metabolism, and antilipemic agents are generally used as drugs. Other drugs administered are antiplatelet agents or anticoagulants for preventing vascular blockage at the site of arteriosclerosis. However, these drugs do not positively treat the rupture of the vascular wall. They are expected to show the indirect action of preventing progression of rupture by holding down hyperlipidemia which is a cause of rupture, or thrombus formation which is a cause of progression of rupture.

For the occurrence or progression of arteriosclerosis, injury or functional loss of vascular endothelial cells is considered important and indispensable. With conventional therapies, as stated earlier, only the repairing function of the body has been relied on for elimination of the radical cause of vascular rupture, the most important measure for treatment, i.e., the regeneration and functional restoration of vascular endothelial cells. Hence, "vascular endothelium regeneration therapy", a therapy for promoting the regeneration and functional restoration of vascular endothelial cells which have undergone damage and lost their intrinsic functions, is believed to be a very useful therapy capable of overcoming the drawbacks of conventional therapies. However, drugs usable for the vascular endothelium regeneration therapy have not been put to practical use, and the development of high quality drugs is desired. An example of the vascular endothelium regeneration therapy was presented by a report (Asahara, T. et al., Circulation, 94, 3291, 1996) of a study in which a gene for vascular endothelial growth factor (VEGF) was introduced at the vascular endothelial injury site of an experimentally injured rabbit to express VEGF, and its efficacy was investigated.

Percutaneous transluminal coronary angioplasty (PTCA) is a method for inflating a balloon catheter inserted into the blood vessel (i.e., ballooning) to dilate the site of narrowing formed as a result of progression of arteriosclerosis. This method is one of the established therapies of coronary arteriosclerosis. However, restenosis was noted in 30 to 50% of patients within 6 months after operation, and so this method has posed a major problem. Restenosis is said to be a kind of arteriosclerosis which is caused by ballooning, and progresses rapidly. In addition to contrivances for ballooning techniques and improvements on catheters, treatments using various drugs have so far been tried. They are still insufficient, and the development of better therapies and drugs is expected. The vascular endothelium regeneration therapy may be able to prevent post-PTCA restenosis effectively (see the report by Asahara et al.), and the development of excellent drugs used for this therapy is expected.

Prognoses of ischemic diseases, such as myocardial infarction, are affected by many factors, and the degree of collateral vessels development has been thought to be one of the most important determinant factors for prognosis. In the presence of a sufficient development of collateral vessels, even if stenosis or blockage (infarction) occurs, ischemia or necrosis of tissue is suppressed, and reduction of an infarct size and improvement of prognosis are achieved. As mechanisms of collateral vessel formation, changes in intravascular pressure and bloodstream have been emphasized. However, there have been reports of images of cell division accompanied by DNA synthesis observed in vascular endothelial cells or vascular smooth muscle cells during collateral vessel formation. It is understood that the process of collateral vessel formation is not simply the dilatation of the existing anastomosed blood vessels by physical factors, but at least part of the process is a neovascularization process which the growth of cells constituting a vessel wall is involved in. In recent years, there have been attempts to treat ischemic heart disease by a new therapy called "angiogenic therapy" (e.g., Yanagisawa-Miwa, A. et al., Science, 257, 1401, 1992). Angiogenic therapy is an attempt to promote angiogenesis around ischemic tissue, thereby positively securing a collateral vessel and protecting the ischemic tissue. It is a new therapy which can be called "pharmacological bypass therapy". However, this therapy has not been put to practical use, and the development of excellent drugs and therapeutic methods usable for it is expected. The attempt to utilize angiogenic growth factors (e.g., fibroblast growth factor) for the treatment of wounds has also been made (see, for example, Hockel, M. et al., Arch. Surg., 128, 423, 1993).

Artificial organs are designed to supplement or replace the functions of various living tissues and organs, such as heart, blood vessel, cardiac valve, lung, pancreas, kidney, liver, skin, and mucosa, by molded products using artificial materials, or devices using them as components. The artificial organ shows its function when implanted in vivo or when contacted with blood withdrawn by cannulation into the blood vessel. Thus, a material used for it must have the nature of being usable without doing harm to the body, namely, biocompatibility. The most important in vivo reaction that defines the biocompatibility of an artificial organ is a thrombus formation reaction.

Platelet adhesion and aggregation are among important biological reactions which take part in the thrombus formation reaction, ranking with the activation of blood coagulation proteins. These reactions are present for hemostatic function indispensable to the normal in vivo defense system. There is also the possibility that when blood contacts an artificial organ, thrombus formation mediated by platelet adhesion and aggregation takes place. Upon thrombus formation, the artificial organ cannot perform its inherent function. To avoid disadvantages such as thrombus formation, it has been attempted to develop materials which cause neither adhesion nor aggregation of platelets, namely, antithrombotic materials. Various studies have been conducted energetically, but the studies of materials are still unsatisfactory. Development of better antithrombotic materials indispensable to the development of excellent artificial organs is expected.

To avoid thrombus formation, it has been attempted to develop materials which cause no formation of thrombus upon contact with blood, namely, antithrombotic materials. What directly touches the blood in the body are vascular endothelial cells constituting the vascular endothelium, and no thrombus is formed on the normal vascular endothelial cell. As a matter of course, the best antithrombotic material is a vascular endothelial cell, a natural antithrombotic material. If the surface of an artificial organ in contact with the blood is coated with a vascular endothelial cell as is the intact organ, no thrombus formation reaction takes place. As an attempt to develop an artificial organ positively utilizing the antithrombotic properties of the vascular endothelial cell, clinical application of a neogenetic intimal healing promoting artificial blood vessel, etc. has been attempted, with some successful results (e.g., Noishiki, Y. et al., Trans. Am. Soc. Artif. Intern. Organs., 27, 309, 1986). Approaches have been taken, such as the use of highly cytophilic materials, and increases in the porosity of molded products for promotion of cell penetration. However, there have been few attempts to promote coating with vascular endothelial cells by use of a substance which promotes the growth of these cells.

Besides artificial organs, medical devices having opportunities to contact blood should desirably use antithrombotic materials, because it is disadvantageous if their contact with blood causes platelet adhesion and aggregation. For these reasons as well, development of better antithrombotic materials is expected.

Furthermore, substances having the action of promoting growth of vascular endothelial cells can be used as materials for cell culture compositions or cell culture equipment.

DISCLOSURE OF THE INVENTION

As is clear from the foregoing descriptions, it is an important challenge for medical practice to provide an excellent antithrombotic agent and an excellent antithrombotic material.

Moreover, it is an important challenge for medical practice and experiments in cell biology to provide an excellent vascular endothelial cell growth promoting substance and an excellent high molecular substance having vascular endothelial cell growth promoting activity.

To meet these challenges, the inventors of the present invention conducted extensive studies. As a result, they found that compounds of the general formula (1), pharmacologically acceptable salts and solvates of the compounds, or solvates of the salts have an excellent platelet adhesion/aggregation suppressing action. They also found that polymers having the compounds as a side chain structure have an excellent platelet adhesion suppressing action. These findings led them to accomplish the present invention.

The inventors also found that the compounds of the general formula (1), the pharmacologically acceptable salts and solvates of the compounds, or the solvates of the salts have an excellent vascular endothelial cell growth promoting action and an excellent angiogenesis promoting action. They further found that high molecular substances having the compounds as a side chain structure have an excellent vascular endothelial cell growth promoting action. These findings led them to accomplish the present invention.

That is, this invention provides compounds of the below-described general formula (1) having a glucuronic acid derivative and a glucosamine derivative in the structure thereof, pharmacologically acceptable salts and solvates of the compounds, or solvates of the salts.

The invention further provides a method for producing the compounds of the general formula (1), characterized by including the step of depolymerizing hyaluronan or its salt.

The invention further provides a pharmaceutical composition containing at least one of the compounds of the general formula (1) as an active ingredient. The pharmaceutical composition is useful for drugs in the treatment and prevention of thrombosis, drugs for treatment and prevention of cardiovascular diseases, drugs for treatment and prevention of cerebrovascular disorders, and drugs for treatment and prevention of peripheral vascular disorders.

The invention further provides an antiplatelet agent containing at least one of the compounds of the general formula (1) as an active ingredient.

The invention further provides a vascular endothelial cell growth promoting agent containing the compound of the general formula (1) as an active ingredient. The vascular endothelial cell growth promoting agent is useful as a therapeutic or preventive drug for vascular endothelium regeneration therapy, or a therapeutic or preventive drug for angiogenic therapy.

The invention further provides polymers having at least one of the compounds of the general formula (1) as a side chain structure.

The invention further provides coating agents containing at least one of the compounds of the general formula (1) or the above polymers as an active ingredient.

The invention further provides molded products using at least one of the polymers as a material.

The invention further provides molded products produced using at least one of the coating agents.

The invention further provides an artificial organ using at least one of the molded products as a component.

The invention further provides a medical device using at least one of the molded products as a component.

The invention further provides a composition for cell culture containing the polymer as an active ingredient.

The invention further provides equipment for cell culture produced using the molded product and/or the coating agent.

BEST MODE FOR CARRYING OUT THE INVENTION

Compounds of the Invention

The compounds of the invention are compounds of the following general formula (1) having a glucuronic acid derivative and a glucosamine derivative in their structure, pharmacologically acceptable salts and solvates of the compounds, or solvates of the salts.

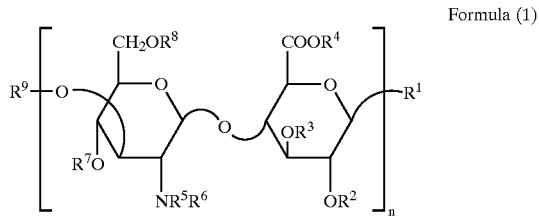

Formula (1)

where
$R^1$ denotes a protective group, or any of the following formulae (2) to (5) where $R^{10}$ denotes a hydrogen atom, a protective group, or any of the following formulae (6) to (8), and $R^{11}$ denotes a hydrogen atom or a protective group, provided that when $R^{10}$ and $R^{11}$ are each a hydrogen atom or a protective group, $R^1$ may be bound in a trans form or cis form with respect to $COOR^4$, —$OR^{10}$      Formula (2)

—$NHR^{11}$,      Formula (3)

—$CH_2R^{11}$,      Formula (4)

—$SR^{11}$,      Formula (5)

Formula (6)

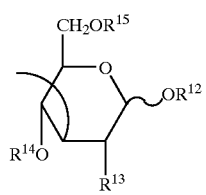

Formula (7)

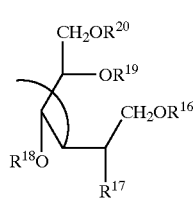

Formula (8)

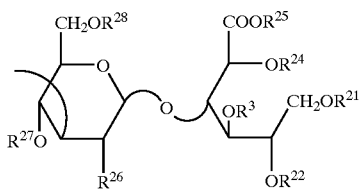

or when $R^{10}$ is any of the formulae (6) to (8), $R^{12}$ to $R^{28}$, except $R^{13}$, $R^{17}$ and $R^{26}$, in the formulae (6) to (8) are the same or different, and each denote a hydrogen atom or a protective group, and $R^{13}$, $R^{17}$ and $R^{26}$ each denote an azido group or the following formula (9)

—$NR^{29}R^{30}$      Formula (9)

where $R^{29}$ and $R^{30}$ are the same or different, and each denote a hydrogen atom or a protective group, $R^2$ to $R^8$ are the same or different, and each denote a hydrogen atom or a protective group, $R^9$ denotes a hydrogen atom, a protective group, or the following formula (10) or (11).

Formula (10)

Formula (11)

where $R^{31}$ to $R^{37}$ are the same or different, and each denote a hydrogen atom or a protective group, and n denotes an integer of 0 to 25, provided that when n is 0, $R^1$ is a group of the formula (2), $R^{10}$ is a group of the formula (8), and $R^9$ is a group of the formula (10) or (11), with the proviso that in the formulae (1), (6) to (8), and (10) to (11), the protective groups are the same or different, and each denote an optionally substituted straight chain or branched chain alkyl having 1 to 8 carbon atoms, an optionally substituted.straight chain or branched chain alkenyl having 2 to 8 carbon atoms, an optionally substituted acyl having 1 to 8 carbon atoms, an optionally substituted aromatic acyl, or an optionally substituted aromatic alkyl, any two of the protective groups as $R^2$ to $R^{37}$ except $R^{13}$, $R^{17}$ and $R^{26}$, may together form an optionally substituted alkylidene having 3 to 8 carbon atoms, an optionally substituted cyclic alkylidene having 3 to 8 carbon atoms, an optionally substituted benzylidene, or an optionally substituted phthaloyl, and when n is 2 or more, $R^2$ to $R^8$ may be the same or different in each of the recurring units.

That is, the compounds of the invention expressed by the formula (1) have a structure comprising a D-glucosamine derivative of the formula (12) and a D-glucuronic acid derivative of the formula (13) bound together.

Formula (12)

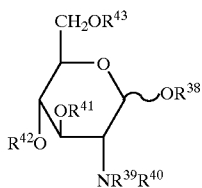

where $R^{38}$ to $R^{43}$ each denote a hydrogen atom or a protective group.

Formula (13)

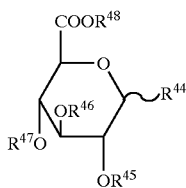

where $R^{44}$ denotes a hydroxyl group or a protective group, and $R^{45}$ to $R^{48}$ each denote a hydrogen atom or a protective group.

In the formula (1), n denotes an integer of 0 to 25, and when n is 0, $R^1$ is a group of the formula (2), $R^{10}$ is a group of the formula (8), and $R^9$ is a group of the formula (10) or (11). That is, the compounds of the formula (1) are expressed by the following formula (14) or (15).

Formula (14)

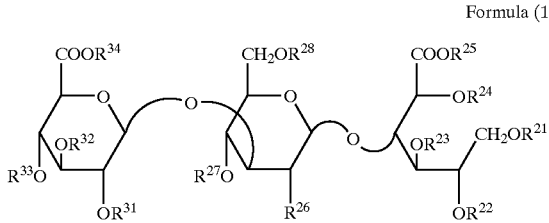

Formula (15)

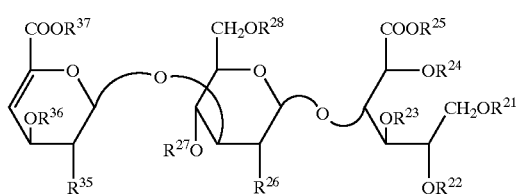

The protective group herein refers to those including various protective groups shown in Theodra W. Green "Productive Groups in Organic Synthesis"; 2nd Ed.; 1991.

The protective groups shown in the formulae (1) to (11) are as follows: Examples of the optionally substituted straight chain or branched chain alkyl having 1 to 8 carbon atoms are methyl, ethyl, propyl, isopropyl, butyl, tertiary butyl, pentyl, octyl, methoxymethyl, tertiary butylthiomethyl, 1-ethoxyethyl, siloxymethyl, and 2-methoxyethoxymethyl. Examples of the optionally substituted straight chain or branched chain alkenyl having 2 to 8 carbon atoms are ethenyl, 1-propenyl, 2-propenyl, butenyl, and octenyl. Examples of the optionally substituted straight chain or branched chain acyl having 1 to 8 carbon atoms are formyl, acetyl, propionyl, butyryl, valeryl or pivaloyl, and haloacyl, examples of the haloacyl being chloroacetyl, dichloroacetyl, trichloroacetyl, and trifluoroacetyl. Examples of the optionally substituted aromatic acyl are benzoyl, and parachlorobenzoyl. Examples of the optionally substituted aromatic alkyl are an optionally substituted benzyl, an optionally substituted diphenylmethyl, or an optionally substituted triphenylmethyl, an example of the optionally substituted benzyl being 4-methoxybenzyl. In connection with the protective groups shown in the formulae (1) to (11), any two of the protective groups as $R^2$ to $R^{37}$, except $R^{13}$, $R^{17}$ and $R^{26}$, may together form one protective group, i.e., an optionally substituted alkylidene having 3 to 8 carbon atoms, an optionally substituted cyclic alkylidene having 3 to 8 carbon atoms, an optionally substituted benzylidene, or an optionally substituted phthaloyl. Examples of the optionally substituted alkylidene having 3 to 8 carbon atoms are propylidene, butylidene, and octylidene. Examples of the optionally substituted cyclic alkylidene having 3 to 8carbon atoms are cyclopentylidene, cyclohexylidene, and cycloheptylidene. Other examples are an optionally substituted benzylidene, and an optionally substituted phthaloyl. Preferred as the protective group for a hydroxyl group is an optionally substituted straight chain or branched chain acyl having 1 to 8 carbon atoms, an optionally substituted aromatic alkyl, an optionally substituted straight chain or branched chain alkenyl having 2 or more carbon atoms, or an optionally substituted benzylidene. More preferred is acetyl, benzyl, 1-propenyl, or benzylidene. Preferred as the protective group for an amino group is an optionally substituted straight chain or branched chain acyl having 1 or more carbon atoms, or an optionally substituted phthaloyl. More preferred is acetyl or phthaloyl. Preferred as the protective group for a carboxyl group is an optionally substituted straight chain or branched chain alkyl having 1 to 8 carbon atoms, or an optionally substituted aromatic alkyl. More preferred is methoxyl, methyl, ethyl, propyl, isopropyl, butyl, isobutyl, pentyl, isopentyl, or diphenylmethyl. The above-described protective groups may be the same or different in the same compound, and can be selected arbitrarily.

In the formula (1), n is an integer of 0 to 25, preferably 0 to 10, and particularly preferably 0 to 5.

$R^9$ may be-that consistent with the foregoing descriptions, and is preferably the formula (11). That is, the compounds of the formula (1) are preferably the following formula (16).

Formula (16)

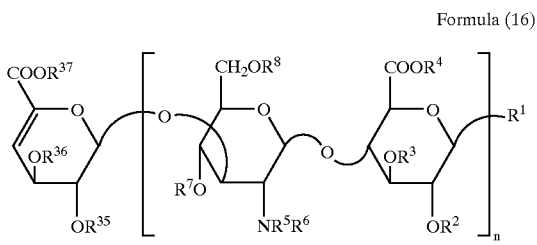

At this time, it is further preferred that in the presence of the formula (11), $R^1$ is any of the formulae (6) to (8), i.e., the compounds of the formula (1) are any of the following formulae (17) to (19).

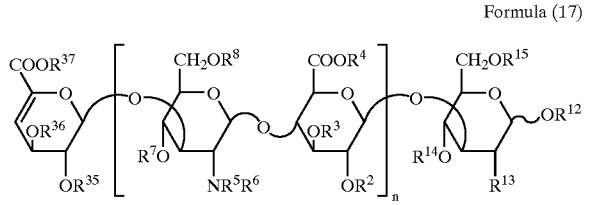

Formula (17)

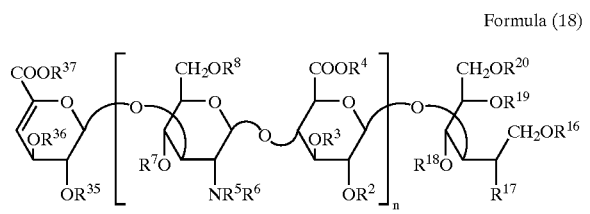

Formula (18)

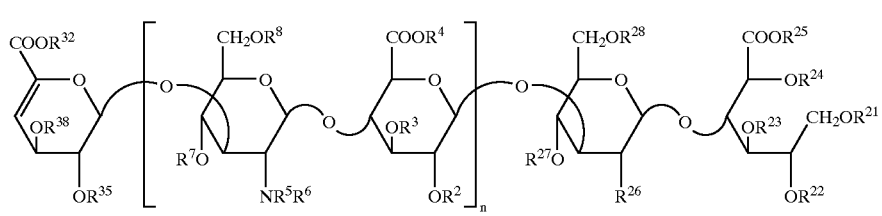

Formula (19)

Furthermore, in the formulae (17) to (19), it is particularly preferred for $R^{13}$, $R^{17}$ and $R^{26}$ to be the formula (9).

The compounds of the invention have two different categories of actions, (A) a platelet adhesion/aggregation suppressing action, and (B) a vascular endothelial cell growth promoting action and a angiogenesis promoting action. When the compounds are to be used for the purpose of (B), the compounds of the formula (16) are particularly preferred.

The pharmacologically acceptable salt herein refers to a salt which exerts no adverse influence on the body when the compound of the invention is administered in a therapeutically necessary dose, or a salt which does not impair the effective pharmacological nature of the compound of the invention when this compound is converted into the salt form. Examples of such a salt are salts of alkali metals or alkali earth metals, such as sodium salt, potassium salt and calcium salt; hydrohalogenic acid salts, such as hydrofluoride, hydrochloride, hydrobromide, and hydroiodide; lower alkylsulfonates, such as methanesulfonate, trifluoromethanesulfonate, and ethanesulfonate; arylsulfonates, such as benzenesulfonate, and p-toluenesulfonate; organic acid salts, such as fumarate, succinate, citrate, tartrate, oxalate, and maleate; and amino acid salts, such as glutamate and aspartate. Moreover, the compounds of the invention and their salts include solvates with various pharmacologically acceptable solvents, such as water, organic solvents, and buffers, as well as those which are polymorphic.

The compounds of the invention may have an asymmetric carbon atom, depending on the type of the substituent, and may exist as optical isomers based on the presence of the asymmetric center. Thus, the compounds of the invention include all of respective isomers and their mixtures. For example, the compounds include mixtures of certain optical isomers and their enantiomers, especially racemic modifications which are mixtures of equal amounts of D and L isomers, or mixtures of certain optical isomers and their diastereomers.

Methods for Producing the Compounds of the Invention

Needless to say, various methods are available for obtaining the compounds of the invention. Examples of such methods are organic chemical methods, namely methods of synthesizing or modifying intermediates or desired compounds by organic chemical techniques using glucuronic acid derivatives and glucosamine derivatives as starting materials, or methods of obtaining intermediates or desired compounds by decomposing polysaccharides with acids or alkalis; biochemical methods, namely methods of synthesizing or modifying intermediates or desired compounds by utilizing reverse reactions of transferases or depolymerization enzymes with the use of glucuronic acid and N-acetylglucosamine as starting materials, or methods of obtaining intermediates or desired compounds by depolymerizating polysaccharides with enzymes; and method involving genetic engineering technologies, namely methods of obtaining starting materials, intermediates or desired compounds, or enzymes for use in synthesis or modification, by introduction of genes for enzymes into microorganisms or cells. These methods are used alone or in combination. It goes without saying that the compounds of the invention are not restricted by these production methods, and any methods can be employed as long as they obtain the desired compounds.

Of the various manufacturing methods, the methods of production using naturally occurring substances, especially polysaccharides or oligosaccharides, as starting materials or intermediates are the most efficient methods, and preferred. Furthermore, it is more preferred to employ a method in which hyaluronan and its salts extracted from animal tissue or cultures of microorganisms, followed by purification if necessary, are used as starting materials, and hyaluronan is depolymerized to obtain depolymerization products, and these products are used as intermediates or desired compounds. Methods of depolymerization may be, for example, physical methods using heat or ultrasonication, chemical methods using acids or alkalis, or biochemical methods using enzymes. These methods may be used alone or in combination. Of these methods, the methods using enzymes are preferred because of the specificity, efficiency or safety of the reaction. The enzymes used may be those having the activity to catalyze the depolymerization reaction of hyaluronan, and are not restricted. Such enzymes can be used alone or as a combination of plural types, depending on the purpose. Examples of the enzymes are enzymes of animal tissue origin, such as testicular hyaluronidase (EC 3.2.1.35), leech hyaluronidase (EC 3.2.1.36), hyaluronidase in Inimicus japonicus's venom (EC 3.2.1), β-glucuronidase (EC 3.2.1.31), and β-N-acetylhexosaminidase (EC 3.2.1.52), and enzymes of microorganism origin, such as hyaluronidase from Streptomyces hyalurolyticus (EC 4.2.2.1), hyaluronidase SD (EC 4.2.2), chondroitinase ABC (EC 4.2.2.4), chondroitinase AC I (EC 4.2.2.5), and chondroitinase AC II (EC 4.2.2.5). Of these enzymes, the microorganism-originated enzymes are preferred, because of the advantage that they can be supplied stably with stable quality. Of them, the enzyme from Streptomyces hyalurolyticus is particularly preferred.

The enzyme reaction may be performed, with various conditions, such as temperature and pH, being set according to the characteristics of the enzymes. To omit a desalting step which is highly likely to be required in carrying out subsequent fractionation, purification or modification, the reaction is preferably performed in a substantially salt-free state, or in a state substantially free from nonvolatile salts and salts insoluble in organic solvents. The substantially salt-free state refers to a state not containing a salt in an amount exceeding such an amount as will make it possible to easily perform a subsequent fractionation, purification or modification step without performing a desalting step after the enzyme reaction. Preferably, the salt content in the reaction mixture is 10% (w/w) or less, more preferably 1% (w/w) or less of the desired compound. The salts in the reaction mixture herein refer to components of a buffer used for adjustment of ion strength and pH, for example, sodium acetate, sodium phosphate, potassium citrate, sodium chloride, potassium chloride, and calcium chloride. The nonvolatile salts herein refer to salts which are other than volatile salts relatively easily volatilizable by a pressure reducing step, such as ammonium acetate and ammonium bicarbonate. The use of volatile salts makes it possible to remove the salts at the same time as removing liquid components from solutions of the intermediates or desired compounds by pressure reduction or the like. The salts insoluble in organic solvents herein refer to salts which are other than salts soluble not only in water, but also in organic solvents (e.g., ethanol, methanol, and propanol), such as ammonium acetate, sodium acetate, potassium acetate, and calcium acetate. When salts soluble in organic solvents are used, a mixture containing an intermediate or desired compound, which is soluble in water incorporating the salts soluble in organic solvents but which is insoluble in organic solvents, is washed with a suitable organic solvent, whereby the incorporated salts can be easily separated.

The resulting depolymerization product can be separated and purified, where necessary, by a customary method, such as extraction, concentration, filtration, recrystallization, reprecipitation, or chromatography. It is preferred to include the step of separating and purifying by chromatography, more preferably, ion exchange chromatography, because of its high efficiency. It is more preferred to use an anion exchanger as a carrier. The chromatograph is available as a batch type, a circulation type, a moving bed type, or a pseudo-moving bed type, and the optimal one may be selected according to the circumstances. An eluent for use in chromatography may be of the optimal composition according to the method used. To omit a desalting step which is highly likely to be required in carrying out subsequent purification or modification, it is preferred to use an eluent substantially free from nonvolatile salts and salts insoluble in organic solvents. The "eluent substantially free from nonvolatile salts and salts insoluble in organic solvents" refers to an eluent not containing nonvolatile salts or salts insoluble in organic solvents, the salts being in an amount exceeding such an amount as will make it possible to easily perform a subsequent fractionation, purification or modification step without performing a desalting step after chromatography. Preferably, the content of each salt in the eluent is 0.5 M or less, more preferably 0.1 M or less. Normally, the eluent used in ion exchange chromatography contains salts for adjustment of ion strength and pH. When the eluent containing salts is used, it is preferred to use the eluent substantially containing only volatile salts as salts. As the volatile salt, an ammonium salt is preferred in view of the ease of handling, safety, ease of acquisition, and price. Ammonium acetate is further preferred. Alternatively, it is preferred to use the eluent substantially containing only salts soluble in organic solvents as salts. As the salt soluble in an organic solvent, an acetate is preferred in view of the ease of handling, safety, ease of acquisition, and price. Ammonium acetate or sodium acetate is further preferred.

The resulting intermediate can be converted into the desired compound by purification or modification using various methods, for example, organic chemical methods or biochemical methods or combinations of these.

Mode of Administration, Dose and Dosage form of the Compound of the Invention

The compound of the invention, its pharmacologically acceptable salt and solvate, or a solvate of the salt is usually administered systemically or locally, orally or parenterally. As the dose, the optimal dose should be determined according to overall judgment based on conditions, such as the type of disease, the severity of symptoms, the age and body weight of the subject receiving treatment. The dose is not restricted, but in adults, the usual daily dose is 0.01 to 100 mg/kg orally, or 0.001 to 10 mg/kg parenterally. The dose is administered once daily or in divided doses, where necessary.

The compound of the invention, its pharmacologically acceptable salt and solvate, or a solvate of the salt may be administered in any form, such as oral forms including a solid composition, a liquid composition, and other composition, or parenteral forms including injection, externally used preparation, and suppository. The most suitable form is selected according to need. A pharmaceutical composition containing at least one of the compounds of the invention, their pharmacologically acceptable salts and solvates, or solvates of the salts can be prepared by using carriers, excipients and other additives used for ordinary pharmaceutical manufacturing. Examples of the carriers and excipients for preparations are lactose, magnesium stearate, starch, talc, gelatin, agar, pectin, acacia, olive oil, sesame oil, cacao butter, ethylene glycol, and other materials in customary use.

As a solid composition for oral administration, tablets, pills, capsules, powder, and granules are used. In such a solid composition, at least one active substance (active ingredient) is mixed with at least one inert diluent, such as lactose, mannitol, glucose, hydroxypropylcellulose, crystallite cellulose, starch, polyvinylpyrrolidone, or magnesium metasilicate/aluminate. According to the customary method, the composition may contain additives other than the inert diluents, for example, lubricants such as magnesium stearate, disintegrants such as calcium carboxymethylcellulose, and solution adjuvants such as glutamic acid or aspartic acid. Tablets or pills may, if desired, be coated with a sugar coating or a gastric-soluble or enteric-soluble film comprising sucrose, gelatin, hydroxypropyl methylcellulose phthalate or the like. Alternatively, the tablets or pills may be coated with two or more layers. Further, a capsule of an absorbable substance, such as gelatin, is also included.

The liquid composition for oral administration includes pharmaceutically acceptable emulsions, solutions, suspensions, syrups, and elixirs, and may contain generally used inert diluents, such as purified water and ethanol. This composition may contain, in addition to the inert diluents, adjuvants such as wetting agents or suspending agents, sweetening agents, flavoring agents, aromas, and preservatives.

The injection for parenteral administration contain sterile aqueous or nonaqueous solubilizing agents, suspending agents, or emulsifying agents. Examples of the aqueous solubilizing agents and suspending agents are water for injection, and physiological saline for injection. Examples of the nonaqueous solubilizing agents and suspending agents are propylene glycol, polyethylene glycol, vegetable oils such as olive oil, alcohols such as ethanol, and POLYSORBATE 80 (registered trademark). Such a composition may further contain adjuvants, such as preservatives, wetting agents, emulsifying agents, dispersing agents, stabilizers (e.g., lactose), and solution adjuvants (e.g., glutamic acid and aspartic acid). These agents can be sterilized by ordinary sterilizing methods, such as filtration sterilization with a microfiltration membrane, heating sterilization such as moist heat sterilization, or incorporation of a bactericide. Alternatively, a sterile solid composition is produced, and can be used after being dissolved in sterile water or a sterile solvent for injection before being used.

Other pharmaceutical compositions for parenteral administration contain at least one of the compounds of the invention as an active ingredient. They include liquids for external use, ointments, liniments, suppositories, transdermal preparations, and ophthalmic solutions.

Polymer of the Invention and Method for its Production

The polymer of the invention is a high molecular compound having the compound of the invention as a side chain structure, and can be used as a polymeric material having antithrombotic properties. A polymer as a main chain for use in the production of the polymer of the invention is preferably a biocompatible polymer. Examples of such a polymer are polyethylene, polystyrene, polyurethane, polyvinyl chloride, ethylene-vinyl acetate copolymer, polypropylene, polycarbonate, silicone, polymethyl methacrylate, polytetrafluoroethylene, polyethylene terephthalate, polyamide, polysulfone, ABS resin, polyacetal, and derivative of these polymers. A suitable spacer can be inserted between the main chain and the side chain, whereby flexibility can be imparted to the side chain having antithrombotic properties. Alternatively, the polymer may be a block copolymer of a plurality of polymeric compounds having the compound of the invention in a side chain structure. Furthermore, the polymer may have, in addition to the compound of the invention, an antithrombotic substance bound thereto, an example of the antithrombotic substance being a thrombus formation suppressing substance such as heparin, or a thrombolytic enzyme such as urokinase.

As a matter of course, the polymer of the invention is not restricted by the production method, and any method may be adopted, as long as it obtains the desired product. Various methods are available for obtaining the polymer of the invention, and these methods can be used alone or in combination. These production methods are publicly known among people skilled in the art. For example, after the compound of the invention is bound to a monomer for the polymer which will become a main chain, a polymerization reaction may be performed to form the main chain polymer. Alternatively, the compound of the invention may be bonded to the main chain polymer.

The compound of the invention has, in its structure, derivatives of body components, such as a glucuronic acid derivative and a glucosamine derivative. As will be understood from this fact, the compound of the invention is highly biocompatible, and exerts minimal adverse influence on the living body, and exerts minimal adverse influence on the body even if the compound of the invention breaks from the polymer.

Coating Agent and Molded Product of the Invention, and Methods for their Production The invention further provides a coating agent containing at least one of the compounds of the invention as an active ingredient, and a coating agent containing at least one of the polymers of the invention as an active ingredient. Such coating agents can be coated by dissolving or dispersing the compound or polymer of the invention in a suitable solvent, and applying the resulting solution or dispersion to an artificial organ or a medical device by a method such as coating, impregnation, or spray coating.

The molded product of the invention is produced by using at least one of the compounds or polymers of the invention as a material, and is manufactured according to the purpose of use. Hence, the molded product may be prepared by any method, unless the essential nature of the material is impaired. To obtain the molded product of the invention, various methods are available, such as the coating of the compound or polymer onto a separately produced molded product; the bonding of the compound to a separately produced molded product; and direct molding from a material containing the compound or polymer. These methods can be used alone or in combination.

Since the molded product of the invention has high antithrombotic properties, it can be used as a component for an artificial organ or a medical device, or can be used as the artificial organ or medical device itself. The shape of the molded product depends on the nature of the material used, and may be one of the following: film, membrane, tube, plate, net, fiber, or cloth, according to the purpose of use.

Artificial Organ of the Invention and Method for its Production

The artificial organ of the invention is produced by using at least one of the compounds or polymers of the invention as a material, or by using at least one of the molded products of the invention as a component. It is manufactured according to the purpose of its use. It can also be produced by coating the coating agent of the invention onto the so produced artificial organ, or a conventional artificial organ produced by other method. Thus, the artificial organ may be produced by any method, unless the essential nature of the material or component is impaired.

Examples of the artificial organ of the invention are an artificial blood vessel, an artificial heart, a cardiac pacemaker, a prosthetic cardiac valve, an artificial kidney, an artificial lung, an artificial heart-lung machine, an artificial pancreas, an artificial bone, an artificial joint, and an artificial ligament.

Medical Device of the Invention and Method for its Production

The medical device of the invention is produced by using at least one of the compounds or polymers of the invention as a material, or by using at least one of the molded products of the invention as a component. It is manufactured according to the purpose of its use. Thus, the medical device may be produced by any method, unless the essential nature of the material or component is impaired.

Examples of the medical device of the invention are an injection syringe, an injection needle, an indwelling needle for dialysis, an indwelling needle, an infusion set, an infusion/blood filter, a blood bag, a tube catheter (for nutrition, for stomach/esophagus, for bile duct, for respiration, for urology for blood, for heart, for aspiration/injection/drainage, etc.), a hemodialyzer housing, a hemodialyzer hollow yarn, a hemodialysis membrane, an extracorporeal circulation blood circuit, an external shunt, an artificial lung membrane, a wound coating material, and a stent.

Composition for Cell Culture of the Invention

The composition for cell culture according to the invention can be produced by adding the compound of the invention or a polymer, which has at least one of the compounds of the invention as a side chain structure, to a conventional composition for cell culture. Examples of a culture medium for cell culture, to which the compound of the invention or the polymer having at least one of the compounds of the invention as a side chain structure is added, are, but not restricted to, 199 medium, MEM (Eagle's minimum essential medium), BME (Eagle's basal medium, DMEM (Dulbecco-modified Eagle's medium), RPMI1640, Ham's F12 medium, MCDB104, and MCDB153. Cells which can be cultured using the composition for cell culture of the invention include, but are not restricted to, vertebrate cells, such as fish cells, amphibian cells, bird cells, and mammal cells. The compound of the invention has a marked vascular endothelial cell growth promoting action, and a marked angiogenesis promoting action. Thus, the composition for cell culture of the invention can be used for culture of mammal cells, especially vascular endothelial cells, for the purpose of culture for tests and research. The composition can also be utilized for the production of a useful substance such as cell growth factor (e.g., VEGF), as well as for the production of a therapeutic tissue, such as an artificial cultured skin for healing burns.

Equipment for Cell Culture of the Invention

The equipment for cell culture according to the invention is produced by using at least one of the compounds or polymers of the invention as a material, or by using at least one of the molded products of the invention as a component. It is manufactured according to the purpose of its use. It can also be produced by coating the coating agent of the invention onto the so produced equipment for cell culture, or to a conventional equipment for cell culture produced by other method. Thus, the equipment may be produced by any method, unless the essential nature of the material or component is impaired.

Examples of the equipment for cell culture of the invention are a petri dish, a flask, a microplate, and a bottle.

Platelet Aggregation Suppressing Action and Platelet Adhesion Suppressing Action of Compound and Polymer of the Invention The platelet aggregation suppressing action of the compounds of the invention (Compound Examples 1, 2, 3, 4, 6, 8, 10) was measured in accordance with the methods of Born and O'Brien (Born, G., V., R.: Nature (London), 194, 924 (1962)., O'Brien, J., R.: J. Clin. Pathol., 15, 556 (1962)) using rabbit platelet rich plasma. As a control for comparison, the same test was conducted on ticlopidine hydrochloride, an antiplatelet agent. As a result, the compounds of the invention all exhibited a marked platelet aggregation suppressing action in low concentrations.

The platelet adhesion suppressing action of polymeric compounds (Polymer Examples 2 to 4) having the compound of the invention as a side chain structure was evaluated by the microsphere column method (Kataoka, K., Maeda, M., Nishimura, T., Nitadori, Y., Tsuruta, T., Akaike, T., Sakurai, Y.: J. Biomed. Mater. Res., 14, 817 (1980).) using rabbit platelet rich plasma. As a result, the polymers of the invention exhibited a marked platelet adhesion suppressing action.

Furthermore, a molded product having the compound of the invention fixed thereto was obtained by reacting the compound of the invention with a polyethyleneimine activated polyethylene tube, and the platelet adhesion ratio of the molded product was measured. Platelet adhesion was not detected at all, in comparison with the untreated tube to which the compound of the invention was not fixed. The molded product was found to show excellent antithrombotic properties.

Vascular Endothelial Cell Growth Promoting Action of the Compounds and Polymers of the Invention The vascular endothelial cell growth promoting action of the compounds of the invention was measured using bovine aortic endothelial cells. As a result, the compounds of the invention used in the test all showed an excellent growth promoting action in low concentrations. Also, the compounds of the invention acted synergistically with vascular endothelial growth factor (VEGF), a cytokine known to act specifically on vascular endothelial cells and promote the growth of these cells, thereby showing a better vascular endothelial cell growth promoting action. This is proof that the compounds of the invention act synergistically with body-originated intrinsic VEGF and extrinsic VEGF, which has been administered or induced for therapeutic purposes, thereby exhibiting a better vascular endothelial cell growth promoting action.

Bovine aortic endothelial cells were cultured in microplates coated with the above polymers used in the invention, and a vascular endothelial cell growth promoting action was measured. As a result, the polymers of the invention (molded products of the invention) all showed an excellent growth promoting action.

Angiogenesis Promoting Action of the Compounds of the Invention

The angiogenesis promoting action of the compounds of the invention was measured using bovine aortic endothelial cell. As a result, the compounds of the invention all showed an excellent angiogenesis promoting action.

EFFECTS OF THE INVENTION

The compounds of the general formula (1), pharmacologically acceptable salts and solvates of the compounds, or solvates of the salts have an excellent platelet adhesion/aggregation suppressing action, and are useful as therapeutic agents based on this action, i.e., as antiplate let agents. Concretely, they can be used in treatment for the inhibition of progression of thrombosis, prevention of recurrence, secondary prevention of thrombosis in patients having risk factors for thrombosis, and primary prevention of thrombosis in healthy people. More concretely, they are effective for treatment and prophylaxis of cardiovascular diseases (acute myocardial infarction, unstable angina, chronic stable angina, old myocardial infarction, thromboembolism due to atrial fibrillation, disseminated intravascular coagulation syndrome (DIC), graft obstruction after coronary bypass operation, coronary stenosis and obstruction after percutaneous transluminal coronary angioplasty (PTCA), thrombotic complications after prosthetic cardiac valve replacement (thromboembolism, thrombosed valve), pulmonary thromboembolism, activation of platelets in extracorporeal circulation blood), cerebrovascular disorders (transient cerebral ischemic attack (TIA), cerebral infarction), peripheral arterial obstruction (obstructive arteriosclerosis, obstructive thromboanguitis, obstruction after revascularization), glomerular nephritis, nephrotic syndrome, and other thromboses (essential thrombocythemia, thrombotic thrombocytopenic purpura (TPP), hemolytic uremic syndrome, anti-phospholipid antibody syndrome, Kawasaki disease, eclampsia, Behcet disease). The invention also provides a method for production which is useful in producing such excellent compounds.

The compounds of the general formula (1), especially the compounds of the formula (16), pharmacologically acceptable salts and solvates of the compounds, or solvates of the salts have an excellent vascular endothelial cell growth promoting action, and an excellent angiogenesis promoting action. They are useful as therapeutic agents based on these actions. Concretely, they are useful as therapeutic agents and prophylactic agents used for vascular endothelium regeneration therapy or angiogenic therapy (vascular endothelial cell growth promoters, angiogenesis promoters). More concretely, they are effective for treatment and prophylaxis of cardiovascular diseases (acute myocardial infarction, unstable angina, chronic stable angina, old myocardial infarction, thromboembolism due to atrial fibrillation, disseminated intravascular coagulation syndrome (DIC), graft obstruction after coronary bypass operation, coronary stenosis and obstruction after percutaneous transluminal coronary angioplasty (PTCA), thrombotic complications after prosthetic cardiac valve replacement (thromboembolism, thrombosed valve), pulmonary thromboembolism, cerebrovascular disorders (transient cerebral ischemic attack (TIA), cerebral infarction), peripheral arterial obstruction (obstructive arteriosclerosis, obstructive thromboangiitis, obstruction after revascularization), glomerular nephritis, nephrotic syndrome, and other thromboses (essential thrombocythemia, thrombotic thrombocytopenic purpura (TPP), hemolytic uremic syndrome, anti-phospholipid antibody syndrome, Kawasaki disease, eclampsia, Behcet disease); and treatment of wounds (chronic dermal ulcers including decubitus, diabetic ulcer, burns, corneal wound, oral mucositis in cancer patients receiving chemotherapy or radiotherapy, wounds after various operations such as skin graft, injuries of gastrointestinal tissue, etc.).

The compounds and polymers of the invention have excellent antithrombotic properties. Thus, they are useful as materials or coating agents for preparing molded products which require antithrombotic properties.

The compounds, polymers and molded products of the invention have excellent antithrombotic properties. Thus, they are useful as components for artificial organs and medical devices which require antithrombotic properties, or as the artificial organs and medical devices themselves. Concretely, they are useful as materials and components for artificial organs such as an artificial blood vessel, an artificial heart, a cardiac pacemaker, a prosthetic cardiac valve, an artificial kidney, an artificial lung, an artificial heart-lung machine, an artificial pancreas, an artificial bone, an artificial joint, and an artificial ligament; and medical devices such as an injection syringe, an injection needle, an indwelling needle for dialysis, an indwelling needle, an infusion set, an infusion/blood filter, a blood bag, a tube catheter (for nutrition, for stomach/esophagus, for bile duct, for respiration, for urology, for blood vessel, for heart, for aspiration/injection/drainage, etc.), a hemodialyzer housing, a hemodialyzer hollow yarn, a hemodialysis membrane, an extracorporeal circulation blood circuit, an external shunt, an artificial lung membrane, a wound coating material, and a stent.

The compounds of the invention, and polymers having them as a side chain structure have an excellent vascular endothelial cell growth promoting action, and promote coating with vascular endothelial cells. Thus, they are useful as materials or coating agents for preparing molded products which require antithrombotic properties. Besides, these compounds, polymers, and molded products have an excellent vascular endothelial cell growth promoting action, and promote coating with vascular endothelial cells. Thus, they are useful as components for artificial organs and medical devices which require antithrombotic properties, or as the artificial organs and medical devices themselves.

Furthermore, the compounds of the invention, or polymers having at least one of the compounds as a side chain structure are useful as ingredients for compositions for cell culture. The compounds of the invention, and polymers having the compounds as a side chain structure can be expected to be utilized as equipment for cell culture.

EXAMPLES

In the Examples to follow, the present invention will be described in greater detail by way of Compound Production Examples, Polymer Production Example, Molded Product Production Example, Antithrombotic Action Tests, and Preparation Production Example. Needless to say, the invention is not restricted to the substances, formulations and methods described in the following examples, and includes all the substances, formulations and methods included in the scope of the claims.

Example 1

Compound Production Example 1

Production of 4-deoxy-α-L-threo-hexa-4-enepyranuronosyl-(1→3)-O-2-acetamide-2-deoxy-β-D-glucopyranosyl-(1→4) -3-O-β-D-glucopyranuronosyl-(1→3)-O-2-acetamide-2-deoxy-β-D-glucopyranose [ΔHexA β1→3GlcNAc β1→4GlcA β1→3GlcNAc (Compound Example 1)], 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(14)-3-O-β-D-glucopyranuronosyl-(1→3)-O-2-acetamide-2-deoxy-β-D-glucopyranose [ΔHexA β1→3GlcNAc β1-4GlcA β13GlcNAc β1→4GlcA β1→3GlcNAc (Compound Example 2)], 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D- glucopyranose [ΔHexA β1→3GlcNAc β1→4GlcA β1→3GlcNAc β1→4GlcA β1→3GlcNAc β1→4GlcA β1→3GlcNAc (Compound Example 3)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-actamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc β1→4GlcA β1→3GlcNAc β1→4GlcA β1→3GlcNAc (Compound Example 4)].

30 g of sodium hyaluronate (a product of KIBUN FOOD CHEMIFA; trade name "Hyaluronic acid FCH") was dissolved in 3 L of distilled water, and the solution was heated to 40° C. The pH of the solution was adjusted to 6.0 with an aqueous solution of 0.1 M sodium hydroxide. Then, hyaluronidase of Streptomyces hyalurolyticus origin (a product of Amano Pharmaceutical; trade name "Hyaluronidase Amano"") was added to a turbidity decrease unit of 0.5 per mg of sodium hyaluronate, and the reaction was performed for 100 hours at 40° C. After the reaction, the enzyme was removed from the solution by an ultrafiltration membrane (a product of Millipore) of hydrophilic polyethersulfone with a nominal molecular cutoff of 10 k. The solvent was removed by lyophilization to obtain a depolymerization product (27.4 g).

The depolymerization product was fractionated by anion exchange chromatography (column: YMC-Pack IEC-AX, eluent: A; water, B; 0.4M NaCl; linear gradient (30 min), detection: UV (232 nm)) (Compound Examples 1, 2, 3 and 4 were eluted in this order) to obtain fractions containing Compound Examples 1 to 4. The respective fractions were desalted by gel filtration (gel: Sephadex G-10, eluent: water), and then lyophilized to obtain Compounds 1 to 4 (white powder). The yields were Compound Example 1: 1.7 g, Compound Example 2: 5.9 g, Compound Example 3: 3.4 g, and Compound Example 4: 2.2 g, respectively. The respective compounds were obtained as sodium salts.

Compound Examples 1 to 4 are compounds expressed by the following formula (20) where n denotes an integer of 1 to 4. This formula represents Compound Example 1 when n is 1, Compound Example 2 when n is 2, Compound Example 3 when n is 3, and Compound Example 4 when n is 4.

Formula (20)

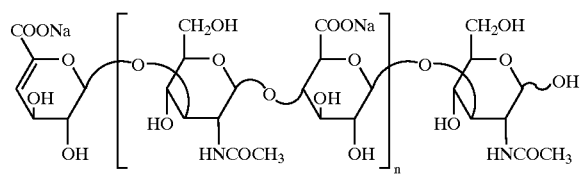

The purity of each of the compounds measured by high performance liquid chromatography (column: TSKgel DEAE-5PW, eluent: A; water, B; 0.3M NaCl; linear gradient (20 min), detection: UV (232 nm); area percentage method) was 97% or more. The uronic acid content of each of Compound Examples 1 to 4 was analyzed by the method of Bitter and Muir (Bitter, T., Muir, H.: Anal. Biochem., 4, 330 (1962)) using glucuronolactone as a standard product. The hexosamine content of each of Compound Examples 1 to 4 was analyzed by the method of Boas (no resin treatment; Boas, N., F.: J. Biol. Chem., 204, 553 (1953).) using glucosamine hydrochloride as a standard product after 16 hours of hydrolysis at 100° C. in 3N hydrochloric acid. The values of the respective compound examples found by analysis nearly agreed with the theoretical values.

Example 2

Compound Production Example 2

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc (Compound Example 1)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranose [ΔHexA β1→3GlcNAc β1→4GlcA β1→3GlcNAc β1→4GlcA β1→3GlcNAc (Compound Example 2)].

60 g of sodium hyaluronate (a product of KIBUN FOOD CHEMIFA; trade name "Hyaluronic acid FCH") was dissolved in 3 L of distilled water, and the solution was heated to 40° C. The pH of the solution was adjusted to 6.0 with an aqueous solution of 0.1 M sodium hydroxide. Then, hyaluronidase of Streptomyces hyalurolyticus origin (a product of Amano Pharmaceutical; trade name "Hyaluronidase Amano"") was added until a turbidity decrease unit of 1 per mg of sodium hyaluronate, and the reaction was performed for 100 hours at 40° C. After the reaction, the enzyme was removed from the solution by an ultrafiltration membrane (a product of Millipore) of hydrophilic polyethersulfone with a nominal molecular cutoff of 10 k. The solvent was removed by lyophilization to obtain a depolymerization product (53.7 g).

The depolymerization product was fractionated by anion exchange chromatography (column: TSKgel DEAE-5PW, eluent: A; water, B; aqueous solution of 0.5M sodium acetate; linear gradient (A/B (90/10)→A/B (60/40); 40 min), detection: UV (232 nm)) (Compound Examples 1 and 2 were eluted in this order) to obtain fractions containing Compound Examples 1 and 2. The respective fractions were lyophilized to remove water. The lyophilized fractions were washed with ethanol for desalting, dissolved in water again, and then lyophilized to obtain Compound Examples 1 and 2 (white powder). The yields were Compound Example 1: 18.1 g, and Compound Example 2: 29.5 g, respectively. The respective compounds were obtained as sodium salts.

The purity of each of the compounds measured by high performance liquid chromatography (column: TSKgel Amide-80, eluent: acetonitrile/water/acetic acid/triethylamine (65/35/2/1, v/v), flow velocity: 1.0 mL/min, column temperature: 80° C., detection: UV (232 nm); area percentage method) was 97% or more. The uronic acid content and hexosamine content of each of Compound Examples 1 and 2 were analyzed by the methods shown in Example 1. The values found nearly agreed with the theoretical values.

Example 3

Compound Production Example 3

Production of 4-deoxy-α-L-threo-hexa-4-enepyranuronosyl-(1→3)-O-2-acetamide-2-deoxy-β-D- glucopyranosyl-(1→4)-3-O-β-D-glucopyranuronosyl-(1→3)-O-2-acetamide-2-deoxy-β-D-glucopyranitol [ΔHexA β1→3GlcNAc β1→4GlcA β1→3GlcNAc OH (Compound Example 5)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranitol [ΔHexA β1→3GlcNAc β1→4GlcA β1→3GlcNAc β1→4GlcA β1→3GlcNAc OH (Compound Example 6)].

50 mg of Compound Example 1 was dissolved in 50 mL of an aqueous solution of 3 mg/mL sodium borohydride, and the solution was treated for 1 hour at room temperature. 5 mL of 6 M acetic acid was added to terminate the reaction. After 50 mL of methanol was added, the mixture was evaporated to dryness by means of an evaporator. Further, addition of 50 mL methanol and evaporation to dryness were repeated twice. The solid matter remaining after evaporation to dryness was dissolved in 5 mL of water. The solution was desalted by gel filtration in the same manner as in Example 1, and then lyophilized to obtain Compound Example 5 (white powder: 44.7 mg).

In the same manner, Compound Example 6 was obtained using Compound Example 2 as the starting material.

Compound Example 5 and Compound Example 6 are compounds expressed by the formula (21) where n denotes an integer of 1 to 2. This formula represents Compound 5 when n is 1, and Compound 6 when n is 2.

Formula (21)

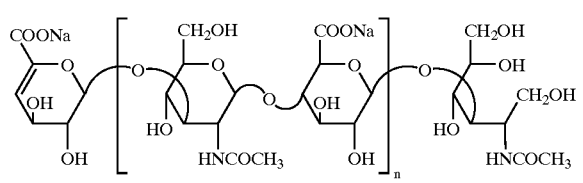

The purity of each of Compounds 5 and 6 was measured by the method shown in Example 2, and found to be 98% or higher. The uronic acid content and hexosamine content of these compounds were analyzed by the methods shown in Example 1. The values found by analysis nearly agreed with the theoretical values.

Example 4

Compound Production Example 4

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronic acid [ΔHexA β1→3GlcNAc β1→4GlcA (Compound Example 7)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronic acid [ΔHexA β1→3GlcNAc β1→4GlcA β1 3GlcNAc 01→4GlcA (Compound Example 8)].

Compound Example 1 was heated in a borate buffer at pH 9 in accordance with the method of Reissig et al. (Reissig, J., L., Strominger, J. L., Leloir, L., F.: J. Biol. Chem., 217, 959 (1953).). Boric acid in the reaction mixture was removed as methyl borate in the same manner as in Example 3. The remaining mixture was desalted by gel filtration in the same manner as in Example 1, and then lyophilized to obtain Compound Example 7 (white powder). When 50 mg of Compound Example 1 was used as the starting material, 43.1 mg of Compound Example 7 was obtained.

Similarly, when 50 mg of Compound Example 2 was used as the starting material, 44.8 mg of Compound Example 8 (white powder) was obtained.

Compound Example 7 and Compound Example 8 are compounds expressed by the formula (22) where n denotes an integer of 0 to 1. This formula represents Compound 7 when n is 0, and Compound 8 when n is 1.

Formula (22)

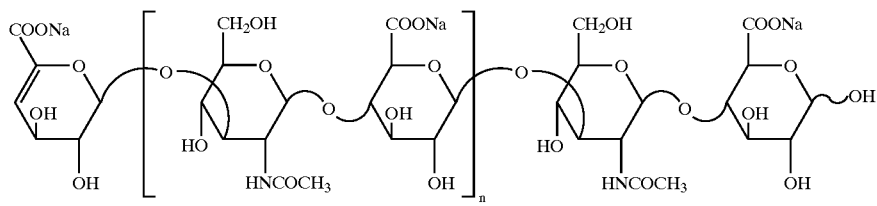

The purity of each of Compound Examples 7 and 8 was measured by the method shown in Example 2, and found to be 98% or higher. The uronic acid content and hexosamine content of these compounds were analyzed by the methods shown in Example 1. The values found by analysis nearly agreed with the theoretical values.

Example 5

Compound Production Example 5

Production of 4-deoxy-α-L-threo-hexa-4-enepyranuronosyl-(1→3)-O-2-acetamide-2-deoxy-β-D-glucopyranosyl-(1→4)-3-O-β-D-glucopyranuronitol [ΔHexA β1→3GlcNAc β1→4GlcA OH (Compound Example 9)], and 4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronitol [ΔHexA β1→3GlcNAc β1→4GlcA β1→3GlcNAc β1→4GlcA OH (Compound Example 10)].

Compound Example 7 was treated in the same manner as in Example 3 to obtain Compound Example 9 (white powder). When 20 mg of Compound Example 7 was used as the starting material, 15.9 mg of Compound Example 9 was obtained.

Similarly, when 20 mg of Compound Example 8 was used as the starting material, 17.8 mg of Compound Example 10 (white powder) was obtained.

Compound Example 9 and Compound Example 10 are compounds expressed by the formula (23) where n denotes an integer of 0 to 1. This formula represents Compound 9 when n is 0, and Compound 10 when n is 1.

Formula (23)

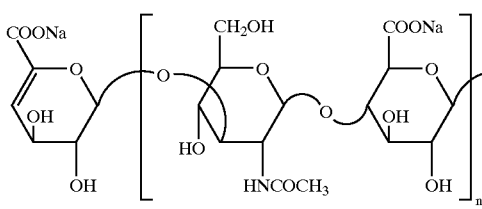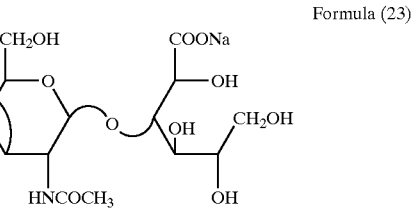

The purity of each of Compounds 9 and 10 was measured by the method shown in Example 2, and found to be 98% or higher. The uronic acid content and hexosamine content of these compounds were analyzed by the methods shown in Example 1. The values found by analysis nearly agreed with the theoretical values.

Example 6

Polymeric Compound Production Example

Production of poly(N-p-vinylbenzyl-[O-4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-gluconamide]) (Polymer Example 1), polyN(-p-vinylbenzyl-[O-4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-gluconamide]) (Polymer Example 2), poly(N-p-vinylbenzyl-[-O-4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-gluconamide]) (Polymer Example 3), and polyN(-p-vinylbenzyl-[O-4-deoxy-α-L -threo-hexa-4-enepyranuronosyl-(13)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-gluconamide]) (Polymer Example 4).

10 g of Compound Example 1 was dissolved in 5 mL of distilled water, and 45 mL of methanol was added, followed by mixing. The mixture was added to a methanol solution of iodine (17.1 g/200 mL) heated to 40° C., and the resulting mixture was allowed to stand for 30 minutes at 40° C. A 4% methanol solution of potassium hydroxide was gradually added until the color of iodine disappeared. The reaction mixture was cooled with ice, and the precipitate formed was collected by filtration. The precipitate was washed with cold ethanol and cold ether in this order, and recrystallized from ethanol-water (90/10, w/w) to obtain a potassium salt. The potassium salt was dissolved in 50 mL of distilled water, and the solution was passed through a column packed with an ion exchange resin (Amberlite IR-12B (H+ type), and then lyophilized. Methanol was added to the lyophilized product, and the mixture was concentrated under reduced pressure to obtain crystals. A small amount of methanol was added to the crystals to dissolve them, and ethanol was further added, followed by dehydration and concentration. This procedure was repeated 5 times, and then the residue was evaporated to dryness under reduced pressure to obtain lactonized Compound Example 1 (7.4g).

7 g of the lactonized Compound Example 1 was dissolved in 50 mL of methanol, and a methanol solution of p-aminomethylstyrene (2.5 g/0.5 mL) was added under reflux with heating. After 120 minutes of heating reflux, 200 mL of acetone was added for crystallization. The crystals were recrystallized twice from methanol to obtain purified crystals (N-p-vinylbenzyl-[O-4-deoxy-α-L-threo-hexa-4-enepyranuronosyl-(1→3)-O-2-acetamide-2-deoxy-β-D-glucopyranosyl-(1→4)-3-O-β-D-glucopyranuronosyl-(1→3)-O-2-acetamide-2-deoxy-β-D-gluconamide]; 3.3 g).

2 g of the purified crystals were dissolved in 2 mL of water, and potassium peroxodisulfate (0.2 mol %) was added as a polymerization initiator. The mixture was heated for 24 hours at 60° C. in a stream of nitrogen to perform a polymerization reaction. After polymerization, the liquid was poured into methanol to precipitate the resulting polymer. Methanol was removed by decantation to separate the polymer. The polymer was subjected to a reprecipitation method in which the polymer was dissolved in water, and crystallized from methanol. As a result, the polymer was purified to obtain Polymer Example 1 (1.4 g).

In the same manner, Polymer Example 2 was obtained using Compound Example 2 as the starting material, Polymer Example 3 was obtained using Compound Example 3 as the starting material, and Polymer Example 4 was obtained using Compound Example 4 as the starting material.

Polymer Examples 1 to 4 are compounds expressed by the formula (24) where n denotes an integer of 1 to 4. This formula represents Polymer Example 1 when n is 1, and Polymer Example 2 when n is 2, Polymer Example 3 when n is 3, and Polymer Example 4 when n is 4.

The weight average molecular weights of Polymer Examples 1 to 4 were measured by the light scattering method, and found to be about 40,000.

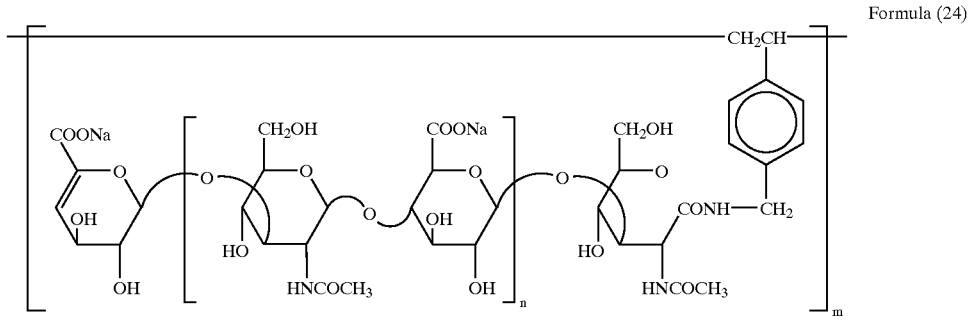

Formula (24)

Example 7

Molded Product Production Example

Production of polyethylene tubes having Compound Examples 1 to 4 fixed thereto (Molded Product Examples 1 to 4).

Production was performed in accordance with the method of Larm et al. (Larm, O., Lasson, R., Olsson, P.: Biomat. Med. Dev. Art. Org., 11, 161 (1983).). Compound Example 1 and a polyethyleneimine activated polyethylene tube (1.8 mm ID×100 cm L) were reacted with NaB(CN)$H_3$ in 0.15 M NaCl for 2 hours at 50° C. and pH 3.5 to obtain a Compound Example 1-fixed polyethylene tube (Molded Product Example 1).

In the same manner, Molded Product Example 2 was obtained using Compound Example 2 as the starting material, Molded Product Example 3 was obtained using Compound Example 3 as the starting material, and Molded Product Example 4 was obtained using Compound Example 4 as the starting material.

Example 8

Platelet Aggregation Suppressing Action of the Compounds of the Invention

Blood was taken from the rabbit aorta in an amount of 9 volumes of the blood per volume of a 3.8% aqueous solution of sodium citrate. The blood sample was immediately centrifuged (50×g, 10 min, room temperature) to obtain platelet rich plasma (PRP) as a supernatant. To 100 µL of PRP, 10 µL of a solution of each of Compounds 1 to 7 of the invention in each concentration. The mixture was held for 1 minute at 37° C., and then 10 µL of 10 µg/mL collagen (bovine tendon collagen: a product of Meiji Yakuhin) was added as an aggregation inducer. An aggregation curve was recorded for 7 minutes after addition. Measurement of platelet aggregation was made in accordance with the methods of Born and O'Brien (Born, G., V., R.: Nature (London), 194, 924 (1962)., O'Brien, J., R.: J. Clin. Pathol., 15, 556 (1962)) using an aggregometer (produced by: MC Medical). As a control for comparison, the same test was conducted on ticlopidine hydrochloride as a representative antithrombotic agent. The results are shown in Table 1.

TABLE 1

| Test Compound | 50% Inhibitory Concentration (µM) |
| --- | --- |
| Compound Example 1 | 2.7 |
| Compound Example 2 | 0.0032 |

TABLE 1-continued

| Test Compound | 50% Inhibitory Concentration (µM) |
| --- | --- |
| Compound Example 3 | 0.0052 |
| Compound Example 4 | 0.0044 |
| Compound Example 6 | 0.0027 |
| Compound Example 8 | 0.0038 |
| Compound Example 10 | 0.0035 |
| Ticlopidine hydrochloride | 427 |

As shown in Table 1, the compounds of the invention exhibited an excellent platelet aggregation suppressing action.

Example 9

Acute Toxicity of the Compounds of the Invention

The representative examples of the compounds of the invention (i.e., Compound Examples 1 to 10) were tested for acute toxicity using rats (weighing 300 to 400 g, Wistar, male). Their $LD_{50}$ values were 500 mg/kg or more.

Example 10

Platelet Adhesion Suppressing Action of the Polymers of the Invention

The platelet adhesion suppressing action of Polymer Examples 2 to 4 was evaluated by the microsphere column method (Kataoka, K., Maeda, M., Nishimura, T., Nitadori, Y., Tsuruta, T., Akaike, T., Sakurai, Y.: J. Biomed. Mater. Res., 14, 817 (1980).). PRP obtained in the same manner as in Example 8 was washed with Dubecco PBS by centrifugation performed twice for 7 minutes at 1,200 G to prepare a t platelet suspension with an end concentration of $1 \times 10^5$ platelets/µL. An aqueous solution of each of the polymers in varying concentration was poured into a microsphere column (Teflon column (3 ID mm×50 mm L) filled with polystyrene beads (diameter 150 µm, 20% divinylbenzene crosslinked, nonporous), and adsorbed. After adsorption, the column was thoroughly rinsed with distilled water. The platelet suspension was passed through this column (flow velocity 0.5 mL/min, room temperature). The platelet concentration in the suspension after its passage was measured, and the platelet adhesion rate was calculated. The results are shown in Tables 2 to 4

TABLE 2

Polymer Example 2

| Concentration (%) | Platelet adhesion rate (%) |
|---|---|
| 0 | 99.7 |
| 0.001 | 90.2 |
| 0.00125 | 63.9 |
| 0.0025 | 28.4 |
| 0.005 | 0 |
| 0.01 | 0 |
| 0.02 | 0 |

TABLE 3

Polymer Example 3

| Concentration (%) | Platelet adhesion rate (%) |
|---|---|
| 0 | 99.6 |
| 0.001 | 91.5 |
| 0.00125 | 62.9 |
| 0.0025 | 29.0 |
| 0.005 | 0 |
| 0.01 | 0 |
| 0.02 | 0 |

TABLE 4

Polymer Example 4

| Concentration (%) | Platelet adhesion rate (%) |
|---|---|
| 0 | 99.8 |
| 0.001 | 90.2 |
| 0.00125 | 60.8 |
| 0.0025 | 27.3 |
| 0.005 | 0 |
| 0.01 | 0 |
| 0.02 | 0 |

As shown in Tables 2 to 4, the compounds of the invention exhibited an excellent platelet adhesion suppressing action.

Example 11

Antithrombotic Properties of the Molded Products of the Invention

The antithrombotic properties of Molded Product Examples 2 to 4 were evaluated. In the same manner as in Example 10, a platelet suspension with an end concentration of $1 \times 10^5$ platelets/RL was prepared. The platelet suspension was passed and circulated through Molded Product Examples 2 to 4 and the untreated polyethylene tube (untreated tube) (flow velocity 0.5 mL/min, 1 hour, room temperature).

The platelet count and concentration in the solution after its passage were measured, and the platelet adhesion rates of the untreated tube and Molded Product Examples 2 to 4 were calculated. The results are shown in Table 5.

TABLE 5

| Test molded product | Platelet adhesion rate (%) |
|---|---|
| Untreated tube | 98.1 |
| Molded Product Example 2 | 0 |
| Molded Product Example 3 | 0 |
| Molded Product Example 4 | 0 |

As shown in Table 5, Molded Product Examples 2 to 4 were clearly lower than the untreated tube in terms of the platelet adhesion rate. This outcome proves that the molded products of the invention have excellent antithrombotic properties.

Example 12

Vascular Endothelial Cell Growth Promoting Action 1 of the Compounds of the Invention This test used bovine aortic vascular endothelial cells (passage number 3) as cells, and MEM containing 10% FCS (fetal calf serum), 100 units/mL penicillin G, and 100 µg/mL streptomycin as a culture medium. 96-Well microplates were seeded with the cells in an amount of $4 \times 10^3$ cells/well ($4 \times 10^4$/mL; 100 µL), and the compounds of the formula (1) (Compound Examples 1 to 10) (10 µL; dissolved in culture medium) were each added in a predetermined end concentration (0, 0.1, 0.5, 1, 5, 10 µg/mL). Culture was performed for 20 hours at 37° C. and 5% $CO_2$, and then the effect of the compounds on vascular endothelial cell growth was measured using "Cell Growth ELISA, BrdU Color Development Kit" (Boehringer Mannheim) (uptake of 5-bromodeoxyuridine (BrdU) was adopted as an indicator).

As controls, Comparative Compounds 1 and 2 were subjected to the same test. The comparative compounds are compounds expressed by the formula (25) where n denotes an integer of 1 or 2. This formula represents Comparative Compound 1 (Comp. 1 in the table below) when n is 1, and Comparative Compound 2 (Comp. 2 in the table) when n is 2. Comparative Compounds 1 and 2 were prepared in accordance with Example 2. However, hyaluronidase was of bovine testicle origin, and detection was performed at 206 nm. The purity of each of the compounds was 97% or higher. The uronic acid content and hexosamine content of these compounds nearly agreed with the theoretical values.

Formula (25)

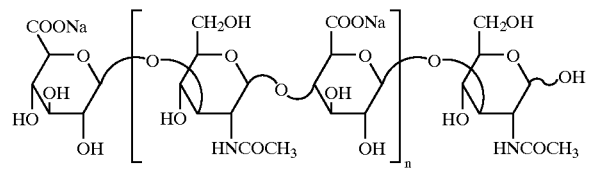

The vascular endothelial cell growth promoting action of each of the compounds was evaluated from the following equation:

Promoting rate (%)={(Increase in the BrdU uptake in the compound addition test)/(Increase in the BrdU uptake in the control test)}×100

The results are shown in Table 6.

TABLE 6

| Compound | Promoting rate (%) Compound concentration ($\mu$g/mL) | | | | |
| --- | --- | --- | --- | --- | --- |
| | 0 | 0.1 | 0.5 | 1 | 5 | 10 |
| 1 | 100.0 | 110.2 | 149.2 | 198.2 | 188.2 | 146.9 |
| 2 | 100.0 | 105.2 | 142.5 | 188.1 | 179.2 | 148.0 |
| 3 | 100.0 | 107.2 | 139.9 | 179.2 | 175.8 | 136.6 |
| 4 | 100.0 | 102.1 | 147.0 | 180.3 | 177.7 | 147.4 |
| 5 | 100.0 | 101.1 | 144.2 | 182.7 | 169.9 | 141.1 |
| 6 | 100.0 | 100.5 | 143.8 | 167.9 | 168.8 | 142.2 |
| 7 | 100.0 | 104.8 | 139.7 | 172.6 | 170.0 | 129.7 |
| 8 | 100.0 | 103.3 | 140.9 | 181.1 | 168.7 | 141.3 |
| 9 | 100.0 | 102.8 | 139.5 | 180.3 | 179.3 | 133.4 |
| 10 | 100.0 | 101.1 | 138.8 | 178.3 | 170.0 | 135.8 |
| Comp. 1 | 100.0 | 100.2 | 98.8 | 111.7 | 100.2 | 101.5 |
| Comp. 2 | 100.0 | 99.5 | 101.1 | 107.3 | 102.0 | 99.2 |

As shown in Table 6, Compound Examples 1 to 10 all showed an excellent vascular endothelial cell growth promotional action.

Example 3

Vascular Endothelial Cell Growth Promoting of the Compounds of the Invention

A test was conducted to investigate the interaction of the compounds of the invention with vascular endothelial growth factor (VEGF). As the VEGF, human recombinant VEGF was used (Vascular Endothelial Growth Factor, Human, Recombinant, For Biochemical Use: a product of Wako Pure Chemical Industries).

The test was conducted in the same manner as in Example 12, but VEGF (final concentration 10 ng/mL) was added simultaneously with the addition of the compound. As comparative tests, a VEGF single addition test (a test in which only VEGF was added) and a negative control test (a test in which neither the compound nor VEGF was added) were performed. The effect on vascular endothelial cell growth was measured in the same way as in Example 12.

The vascular endothelial cell growth promoting action of each of the compounds was evaluated from the following equation:

Promoting rate (%)={(Increase in the BrdU uptake in the compound addition test)/(Increase in the BrdU uptake in the negative control test)}×100

The results are shown in Table 7.

TABLE 7

| Compound | Promoting rate (%) Compound concentration ($\mu$g/mL) | | | | | |
| --- | --- | --- | --- | --- | --- | --- |
| | 0 | 0.1 | 0.5 | 1 | 5 | 10 |
| 1 | 148.5 | 169.8 | 211.2 | 258.3 | 250.2 | 206.8 |
| 2 | 148.5 | 166.2 | 200.6 | 249.5 | 244.0 | 207.8 |
| 5 | 148.5 | 160.9 | 205.0 | 243.8 | 231.1 | 200.4 |
| 6 | 148.5 | 159.8 | 205.2 | 232.2 | 224.8 | 205.7 |
| 7 | 148.5 | 165.0 | 206.2 | 235.9 | 228.7 | 191.3 |
| 8 | 148.5 | 168.7 | 202.9 | 251.2 | 224.9 | 199.2 |
| 9 | 148.5 | 159.8 | 200.2 | 245.6 | 244.2 | 196.8 |
| 10 | 148.5 | 165.2 | 199.9 | 243.3 | 228.7 | 194.0 |

In Table 7, the promoting rates shown in the column for the compound concentration of 0 represent the promoting rates obtained when VEGF was added alone. Based on Table 6 and Table 7 showing the results of the single addition test of the compounds of the invention, the test compounds all acted synergistically with VEGF, and showed an excellent vascular endothelial cell growth promoting action.

Example 14

Angiogenesis Promoting Action 1 of the Compounds of the Invention

One volume of reconstitution buffer (500 mM NaOH, 260 mM $NaHCO_3$, 200 mM HEPES) was mixed with one volume of $NaHCO_3$-free 1/10-concentrated MEM with cooling in an iced water bath. Then, 8 volumes of a 0.3% hydrochloric acid solution of collagen (pH 3.0) was added, followed by thorough mixing, to prepare a collagen solution. The collagen solution (0.5 mL) was dispensed in 24-well microplates, and incubated for 30 minutes at 37° C. for gelation. On the collagen gel, bovine aortic vascular endothelial cells (passage number 3 to 8) were seeded in an amount of $5 \times 10^4$ cells/well. Culture was performed for about 3 hours at 37° C. to cause adhesion of the cells. Then, the culture medium was removed, and 0.5 mL of a collagen solution was overlaid, followed by incubation for 30 minutes at 37° C., to gel the system. Then, 1 mL/well of a 2% FBS-MEM medium containing each of Compound Examples 1 to 4 in varying concentration was added. The mixture was cultured in a $CO_2$ incubator for 3 days at 37° C. After 3 days of culture, blood vessel-like lumina formed (neogenetic blood vessels) were photographed at 100× magnification under a phase contrast microscope. The photographs were traced, and image analyzed using Microcomputer Imaging Device (a product of Neuroscience) to measure the length of the blood vessel-like lumina per unit area. As a control test, the cells cultured in the medium free from the compound were measured for the length of the blood vessel-like lumina in the same manner.

The angiogenesis promoting action of each of the compounds was evaluated from the following equation:

Promoting rate (%)={[(Length of lumina in each test)−(Length of lumina in control test)]/(Length of lumina in control test)}×100

The results are shown in Table 8.

TABLE 8

| Compound | Promoting rate (%) Compound concentration ($\mu$g/mL) | | | | | |
| --- | --- | --- | --- | --- | --- | --- |
| | 0 | 0.1 | 0.3 | 1 | 3 | 10 |
| 1 | 100.0 | 212.1 | 236.4 | 350.1 | 430.3 | 329.7 |
| 2 | 100.0 | 181.8 | 244.9 | 334.2 | 393.9 | 345.5 |
| 3 | 100.0 | 212.1 | 315.2 | 327.3 | 351.5 | 278.8 |
| 4 | 100.0 | 224.2 | 321.2 | 369.9 | 406.1 | 357.6 |

As shown in Table 8, Compounds 1 to 4 all showed an excellent angiogenesis promoting action.

Example 15

Angiogenesis Promoting Action 2 of the Compounds of the Invention

The angiogenesis promoting action of Compound Examples 1 and 2 was evaluated by the diffusion chamber method using rats. That is, a diffusion chamber (membrane pore diameter 0.45 $\mu$m; a product of Millipore) was assembled, and 200 $\mu$L of physiological saline solution of each of Compounds 1 and 2 in varying concentration (0, $10^{-8}$, $10^{-7}$, $10^{-6}$, $10^{-5}$ M) was sealed up therein.

Wistar rats (male, body weight 200 to 250 g) were anesthetized by intraperitoneal administration of pentobarbital (10 mg/animal). Then, the back of the animal was shaved, and disinfected with dilute iodine tincture. The skin was incised without injuring the muscles, and the above solution-sealed diffusion chamber was grafted between a subcutaneous area and the fascia. The site of incision was sutured, and the animal was bred for 1 week. Then, the back of the anesthetized rat was incised to expose the chamber. After the presence of angiogenesis was observed, the chamber was cut off along with the muscle, and fixed in formalin.

The results are shown in Table 4. In the table, +, ±, and — represent that induction of angiogenesis was positive, false positive, and negative, respectively.

TABLE 9

| Compound | Inducing ability Compound concentration (M) | | | | |
|---|---|---|---|---|---|
| | 0 | $10^{-8}$ | $10^{-7}$ | $10^{-6}$ | $10^{-5}$ |
| 1 | − | − | ± | + | + |
| 2 | − | − | − | + | + |

As shown in the table, Compounds 1 and 2 both showed an excellent angiogenesis promoting action.

Example 16

Vascular Endothelial Cell Growth Promoting Action of the Molded Products Produced from the Polymeric Compounds A 0.01 w/v % aqueous solution of each of Polymer Examples 1 to 4 was prepared, and dispensed in 96-well polystyrene microplates in an amount of 0.5 mL/well. The microplates were allowed to stand overnight at room temperature, and then the solution was removed to coat the plates. The coated plates were used to culture bovine aortic vascular endothelial cells in the same manner as in Example 8. As a control test, culture using the uncoated plates was performed. The growth promoting action was measured in the same manner as in Example 12, and the vascular endothelial cell growth promoting action of the Polymer Examples (Molded Products) was evaluated using the following equation:

Promoting rate (%)={((Increase in the BrdU uptake in each test)/ (Increase in the BrdU uptake in the control test)}×100

The results are shown in Table 10.

TABLE 10

| Coated Polymer Example | Promoting Rate (%) |
|---|---|
| 1 | 198.1 |
| 2 | 184.9 |
| 3 | 179.8 |
| 4 | 182.4 |
| Uncoated | 100.0 |

As shown in Table 10, Polymer Examples 1 to 4 all showed an excellent vascular endothelial cell growth promotion action.

Example 16

Preparation Production Example

| Tablet Production 1 | |
|---|---|
| Compound Example 1 | 10 g |
| Polyethylene glycol 6000 | 10 g |
| Sodium lauryl sulfate | 1.5 g |
| Corn starch | 3 g |
| Lactose | 25 g |
| Magnesium stearate | 0.5 g |

The above ingredients are weighed. Polyethylene glycol 600 is heated to 70 to 80° C., and mixed with Compound Example 1, sodium lauryl sulfate, corn starch, and lactose, followed by cooling. The solidified mixture is granulated by means of a grinder to obtain granules. The granules are mixed with magnesium stearate, and then compression tabletted to form tablets with a weight of 250 mg.

| Tablet Production 2 | |
|---|---|
| Compound Example 2 | 30 g |
| Lactose | 55 g |
| Potato starch | 12 g |
| Polyvinyl alcohol | 1.5 g |
| Magnesium stearate | 1.5 g |

The above ingredients are weighed. Compound Example 2, lactose, and potato starch are uniformly mixed. An aqueous solution of polyvinyl alcohol is added to the mixture, and the resulting mixture is made into granules by wet granulation. The granules are dried, and mixed with magnesium stearate. Then, the mixture is compression tabletted to form tablets with a weight of 200 mg.

| Production of capsules | |
|---|---|
| Lactose | 25 g |
| Compound Example 3 | 10 g |
| Corn starch | 5 g |
| Microcrystalline cellulose | 9.5 g |
| Magnesium stearate | 0.5 g |

The above ingredients are weighed. The four ingredients, except magnesium stearate, are uniformly mixed. Magnesium stearate is added, and then the ingredients are further mixed for several minutes. The mixture is filled into No. 1 hard capsules in an amount of 200 mg/capsule, to form capsules.

| Production of powder | |
|---|---|
| Compound Example 4 | 20 g |
| Lactose | 79 g |
| Magnesium stearate | 1 g |

The above ingredients are weighed. All the ingredients are uniformly mixed to form a 20% powder.

| Production of suppository | |
|---|---|
| Compound Example 2 | 10 g |
| Polyethylene glycol 1500 | 18 g |
| Polyethylene glycol 4000 | 72 g |

Compound Example 2 is thoroughly ground on a mortar to form a fine powder, and made into a 1 g rectal suppository by a melting method.

| Production of injection | |
|---|---|
| Compound Example 6 | 0.1 g |
| Sodium chloride | 0.9 g |
| Sodium hydroxide | Suitable amount |
| Water for injection | 100 mL |

The above ingredients are weighed. The three ingredients are dissolved in water for injection, and the solution is sterilized by filtration. Then, the solution is dispensed into 10 mL ampoules in an amount of 5 mL per ampoule. The ampoule is heat sealed to form an injection.

What is claimed is:

1. A compound of the following formula (1), pharmacologically acceptable salts and solvates of the compound, or solvates of the salts:

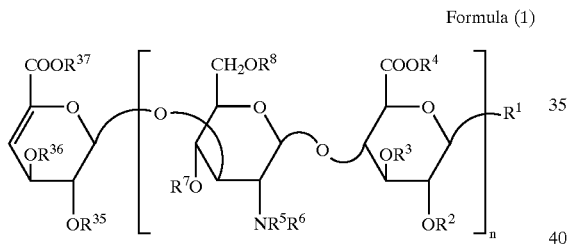

Formula (1)

wherein,

R$^1$ denotes a protective group, or any of the following formulae (2) to (5) where R$^{10}$ denotes a hydrogen atom, a protective group, or any of the following formulae (6) to (8), and R$^{11}$ denotes a hydrogen atom or a protective group, provided that when R$^{10}$ and R$^{11}$ are each a hydrogen atom or a protective group, R$^1$ may be bound in a trans form or cis form with respect to COOR$^4$, —OR$^{10}$  Formula (2)

—NHR$^{11}$,  Formula (3)

—CH$_2$R$^{11}$,  Formula (4)

—SR$^{11}$,  Formula (5)

Formula (6)

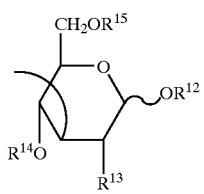

Formula (7)

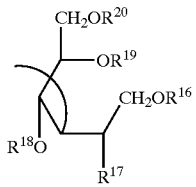

Formula (8)

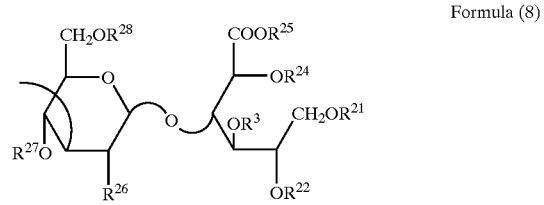

or when R$^{10}$ is any of the formulae (6) to (8), R$^{12}$ to R$^{28}$, except R$^{13}$, R$^{17}$ and R$^{26}$, in the formulae (6) to (8) are the same or different, and each denote a hydrogen atom or a protective group, and R$^{13}$, R$^{17}$ and R$^{26}$ each denote an azido group or the following formula (9)

—NR$^{29}$R$^{30}$  Formula (9)

where R$^{29}$ and R$^{30}$ are the same or different, and each denote a hydrogen atom or a protective group, R$^2$ to R$^8$ are the same or different, and each denote a hydrogen atom or a protective group, R$^{35}$ to R$^{37}$ are the same or different, and each denote a hydrogen atom or a protective group, and n denotes an integer of 0 to 25, provided that when n is 0, R$^1$ is a group of the formula (2), and R$^{10}$ is a group of the formula (8), with the proviso that in the formulae (1) and (6) to (8), the protective groups are the same or different, and each denote an unsubstituted or substituted straight chain or branched chain alkyl having 1 to 8 carbon atoms, an unsubstituted or substituted straight chain or branched chain alkenyl having 2 to 8 carbon atoms, an unsubstituted or substituted acyl having 1 to 8 carbon atoms, an unsubstituted or substituted aromatic acyl, or an unsubstituted or substituted aromatic alkyl, any two of the protective groups as R$^2$ to R$^{37}$, except R$^{13}$, R$^{17}$ and R$^{26}$, may together form an unsubstituted or substituted alkylidene having 3 to 3 carbon atoms, an unsubstituted or substituted cyclic alkylidene having 3 to 8 carbon atoms, an unsubstituted or substituted benzylidene, or unsubstituted or substituted phthaloyl, and when n is 2 or more, R$^2$ to R$^8$ may be the same or different in each of the recurring units.

2. The compound according to claim 1, pharmacologically acceptable salts and solvates of the compounds, or solvates of the salts, wherein n is 0 to 10.

3. The compound according to claim 1, pharmacologically acceptable salts and solvates of the compounds, or solvates of the salts, wherein R$^1$ is the formula (2), and R$^{10}$ is the formula (6).

4. The compound according to claim 3, pharmacologically acceptable salts and solvates of the compounds, or solvates of the salts, wherein R$^{13}$ is the formula (9).

5. The compound according to claim 1, pharmacologically acceptable salts and solvates of the compounds, or solvates of the salts, wherein $R^1$ is the formula (2), and $R^{10}$ is the formula (7).

6. The compound according to claim 5, pharmacologically acceptable salts and solvates of the compounds, or solvates of the salts, wherein $R^{17}$ is the formula (9).

7. The compound according to claim 1, pharmacologically acceptable salts and solvates of the compounds, or solvates of the salts, wherein $R^1$ is the formula (2), and $R^{10}$ is the formula (8).

8. The compound according to claim 7, pharmacologically acceptable salts and solvates of the compounds, or solvates of the salts, wherein $R^{26}$ is the formula (9).

9. A method for producing the compound of claim 1, comprising the step of:

depolymerizing hyaluronan or its salt with an enzyme derived from a microorganism.

10. The method of claim 9, wherein the microorganism is Streptomyces hyalurolyticus.

11. The method of claim 9, wherein the depolymerizing step is performed in a solution substantially free from salts, a solution substantially free from nonvolatile salts, or a solution substantially free from salts insoluble in organic solvents.

12. The method of claim 9, further comprising the step of fractionating and purifying a depolymerized substance by anion exchange chromatography.

13. The method of claim 12, wherein the fractionating and purifying step uses an eluent substantially containing only a volatile salt as a salt.

14. The method of claim 13, wherein the salt is an ammonium salt.

15. The method of claim 14, wherein the ammonium salt is ammonium acetate.

16. The method of claim 12, wherein the fractionating and purifying step uses an eluent substantially containing only a salt soluble in an organic solvent as a salt.

17. The method of claim 16, wherein the salt is an acetate.

18. The method of claim 17, wherein the acetate is ammonium acetate or sodium acetate.

19. A pharmaceutical composition containing at least one of the compounds of claim 1, as an active ingredient and pharmaceutically acceptable carrier.

20. A method for treating a medical condition in a patient, comprising:

administering an effective amount of the pharmaceutical composition according to claim 19.

21. The method for treating a medical condition in a patient according to claim 20, wherein said medical conditions are selected from a group consisting of thrombosis, cardiovascular disease, cerebrovascular disorders and peripheral vascular disorders.

22. An antiplatelet agent containing at least one of the compounds of claim 1 as an active ingredient.

23. A vascular endothelial cell growth promoting agent containing the compound of claim 1 as an active ingredient.

24. A method for vascular endothelial regeneration therapy, comprising the step of administering an effective amount of the agent of claim 23.

25. A method for angiogenic therapy, comprising the step of administering an effective amount of the agent of claim 23.

26. A polymer having at least on side chain structure comprised of the compound of claim 1.

27. A coating agent containing at least one of the polymer according to claim 26 as an active component.

28. A molded product coated with at least one coating agent of claim 27.

29. An artificial organ comprised of at least one of the molded products of claim 28.

30. A medical device comprised of at least one of the molded products of claim 28.

31. A molded product comprising at least one of the polymers of claim 26 as a material.

32. An artificial organ comprised of at least one of the molded products of claim 31.

33. A medical device comprised of at least one of the molded products of claim 31.

34. A composition for cell culture, containing the polymer of claim 26 as an active ingredient.

35. A coating agent containing at least one compound according to claim 1 as an active component.

36. A molded product coated with at least one coating agent of claim 35.

37. An artificial organ comprised of at least one of the molded products of claim 36.

38. The artificial organ of claim 32, 37 or 29, wherein said artificial organ is an extracorporeal circulation artificial organ, or an implantable artificial organ.

39. A medical device comprised of at least one of the molded products of claim 36.

40. The medical device of claim 33, 39 or 30, wherein said medical device is an extracorporeal circulation medical device, extracorporeal circulation medical device connected to the inside of the body of a patient or an implantable artificial organ.

41. An equipment for cell culture, said equipment produced by using the molded products of claim 26 or the coating agents of claim 35 or 37.

\* \* \* \* \*